(12) United States Patent
Pavliv et al.

(10) Patent No.: US 8,722,738 B2
(45) Date of Patent: May 13, 2014

(54) ACETYCYSTEINE COMPOSITIONS AND METHODS OF USE THEREOF

(75) Inventors: Leo Pavliv, Cary, NC (US); Amy Rock, Thompsons Station, TN (US)

(73) Assignee: Cumberland Pharmaceuticals, Inc., Nashville, TN (US)

( * ) Notice: Subject to any disclaimer, the term of this patent is extended or adjusted under 35 U.S.C. 154(b) by 260 days.

(21) Appl. No.: 13/188,152

(22) Filed: Jul. 21, 2011

(65) Prior Publication Data

US 2012/0022161 A1 Jan. 26, 2012

Related U.S. Application Data

(60) Provisional application No. 61/336,439, filed on Jul. 21, 2010.

(51) Int. Cl.
*A61K 31/198* (2006.01)
(52) U.S. Cl.
USPC .......................................... 514/562
(58) Field of Classification Search
None
See application file for complete search history.

(56) References Cited

U.S. PATENT DOCUMENTS

| | | | |
|---|---|---|---|
| 5,691,380 A | 11/1997 | Mason |
| 5,807,894 A | 9/1998 | Stroppolo |
| 6,114,387 A | 9/2000 | Cutler |
| 2007/0049640 A1 | 3/2007 | Pavliv |

OTHER PUBLICATIONS

Merck Index 13th ed., n. 3546, pp. 620-621 (2001).
Merck Index 13th ed., n. 90, p. 17 (2001).
Handbook of Pharmaceutical Excipients, 225-228. (R. Rowe et al. eds), 4th ed. (2003).
Smilkstein et al. Acetaminophen Overdose: A 48-hour intravenous N-acetylcysteine treatment protocol. Annals of Emergency Medicine, 1991, vol. 20, Iss 10, pp. 1058-1063.
Peterson et a. Toxicity of acetaminophen Overdose, Journal of the American College of Emergency Physicians, 1978, vol. 7, Iss 5, pp. 202-205.
Heard, K., Acetylcysteine for Acetaminophen Poisoning. N Engl J Med., 2008, vol. 359(3).
Wolf et al., Clinical Policy; Critial Issues in the Management of Patients Presenting to the Emergency Department with Acetaminophen Overdose Journal of Emergency Nursing, 2008, vol. 34, Iss 2, pp. e1-e18.
Koulouris Z, et al., Metabolic Acidosis and Coma Following a Severe Acetaminophen Overdose. Ann Pharmacother 1999; 33:1191-4.
Intravenous N-Acetylcysteine (Acetadote (R) ) FAQs, Rocky Mountain Poison and Drug Center, Version 7.0, Apr. 6, 2009.
Guidelines for the Management of Acetaminophen Overdose, McNeil Consumer & Specialty Pharmaceuticals, 2000.
International Search Report and Written Opinion of the International Searching Authority, PCT/US2011/44861, Nov. 28, 2011.
Birch, et al.; D2 The Prevention Effect of Acetylcysteine on the Radiographic Contrast Nephropathy; Lance; 2003; 362(9384); 598-603.
Gang, et al.; D1: The Application of N-acetylcysteine in the treatment of liver disease; Chin J Heptatol, 12(3): 185-186, (2004).
Acetadote (R) (Acetylcysteine) Injection Package Insert (NDA 21-539/S-004), (2006).
Parvolex Insert, (2001).

*Primary Examiner* — Bong-Sook Baek
(74) *Attorney, Agent, or Firm* — Stites & Harbison PLLC; Richard S. Myers, Jr.

(57) ABSTRACT

A pharmaceutical composition and method for providing a reduction in side effects for human patients in need of therapy comprising the administration of a pharmaceutical composition comprising acetylcysteine is disclosed.

21 Claims, No Drawings

ACETYCYSTEINE COMPOSITIONS AND METHODS OF USE THEREOF

FIELD OF THE INVENTION

The present invention relates to new acetylcysteine compositions in solution and methods for their use as a treatment and for reducing side effects associated with other known acetylcysteine formulations. In particular, the present invention is directed in part to acetylcysteine compositions which are substantially free of chelating agents, which does not significantly impact the stability of the formulation. In certain embodiments, the invention is directed to a substantially ethylenediaminetetraacetic acid-free (EDTA-free) acetylcysteine composition. In additional/other embodiments, the invention is directed to a new administration regimen for administering acetylcysteine formulations to human patients.

BACKGROUND OF THE INVENTION

Acetadote® (acetylcysteine) Injection was approved for use by the United States (US) Food and Drug Administration (FDA) under a priority drug review in 2004. Acetadote, administered intravenously within 8 to 10 hours after ingestion of a potentially hepatotoxic quantity of acetaminophen, is indicated to prevent or lessen hepatic injury caused by that hepatotoxic quantity of acetaminophen. Acetadote is approved for use in both adults and children.

The approved administration of acetylcysteine Injection involves delivery of 300 mg/kg acetylcysteine in a 3-bag infusion regimen over 21 hours. The amount of product used is determined by the weight of the subject. This current infusion regimen consists of 150 mg/kg over 1 hour; 50 mg/kg over the next 4 hours; and then 100 mg/kg over the next 16 hours. Adverse reactions during the initial infusion may derive in part from the concurrent intravenous delivery of a large amount of acetylcysteine (150 mg/kg per hour) and EDTA (0.375 mg/kg per hour).

Acetylcysteine is an antioxidant having a molecular weight of 163.2 and the following chemical structure: (Merck Index 13$^{th}$ Ed., n90, page 17). Acetylcysteine is marketed generically in the United States and worldwide, as well as under the trade names of Acetadote®, Mucomyst®, Parvolex®, Fluimucil®, and others. It is approved for several indications including treatment of acetaminophen overdose, as an injectable and an oral agent, and as a mucolytic, as an inhalation product. Acetylcysteine is also being used or investigated to treat other indications including liver failure, various cancers, methacrylonitrile poisoning, reduction of radiocontrast-induced nephropathy, and reduction of reperfusion injury during cardio bypass surgery.

Acetylcysteine is not a stable molecule and is oxidized and degraded when in solution and exposed to air. Several U.S. patents have addressed this problem. For example, U.S. Pat. No. 5,691,380 appears to describe the use of a topical silicone-based emulsion system to improve the stability of acetylcysteine.

Other U.S. patents appear to address the problem by using a chelating agent to stabilize the acetylcysteine. Chelating agents, or chelators, can be inorganic or organic agents that bond with and thereby sequester free metal ions from solution. A widely used chelator is edetic acid or ethylenediaminetetraacetic acid, commonly referred to as EDTA, which has a molecular weight of 292.24 and the following chemical structure: (Merck Index 13$^{th}$ ed., n3546, pages 620-621). EDTA is available commercially as the free acid and as various salts, for example disodium EDTA, tetrasodium EDTA, dipotassium EDTA, and calcium disodium EDTA.

U.S. Pat. No. 5,807,894, for instance, appears to describe the use of the chelating agent EDTA to improve the high reactivity of acetylcysteine in a syrup formulation. U.S. Pat. No. 6,114,387 appears to describe the use of EDTA to stabilize acetylcysteine in a solid dosage form. Aqueous solutions of acetylcysteine on the market, such as those under the trade names of Acetadote®, Mucomyst®, Parvolex®, Fluimucil®, also contain EDTA, in the form of the salt disodium edetate, which aids in stabilizing the pharmaceutical product.

While improving the stability of acetylcysteine formulations, chelating agents such as EDTA can cause undesirable effects when administered to humans or animals. Some of these undesirable effects include a significant drop in serum calcium levels (Handbook of Pharmaceutical Excipients 226 (R. Rowe et al. eds., 4$^{th}$ ed., 2003)), which may result in fatality, hypokalemia, hypomagnesemia, hypotension, and EDTA has also been shown to produce reproductive developmental toxicity in test animals. EDTA has also been associated with dose-related bronchoconstriction when used as a preservative in nebulizer solutions. Id. Based on the adverse effects of EDTA, particular care should be taken when administering EDTA to patients with renal impairment, liver toxicity, tuberculosis, and impaired cardiac function. Id.

Since acetylcysteine may be used to prevent or treat a variety of disorders and conditions, including liver damage, the addition of a chelating agent such as EDTA to an acetylcysteine pharmaceutical product is of concern. Chelating agents, while stabilizing the acetylcysteine composition, may also decrease the effectiveness of the composition. In addition, some individuals are allergic to chelating agents such that they cannot receive acetylcysteine compositions containing a chelating agent or may require additional care after receiving such compositions.

It would therefore be desirable to have a stable acetylcysteine solution drug product that does not produce adverse effects upon administration. In certain conditions, such as the use of acetylcysteine to lessen or prevent the liver damage caused by acetaminophen overdose, removing EDTA or other chelating agents could improve efficacy by limiting any additional liver toxicity resulting from the chelating agent.

It would further be desirable to provide an improved method of treatment of patients in need of treatment with acetylcysteine.

SUMMARY OF THE INVENTION

It has been found that an aqueous composition containing acetylcysteine, sterilized water, and a pH-adjusting agent, is stable without the addition of a chelating agent. Thus, the present invention relates to a solution containing acetylcysteine, which is substantially free of chelating agents.

The pH of the aqueous pharmaceutical composition of the invention may be from 5 to 9, from 6 to 8, from 6.5 to 7.0, or 6.8. In certain preferred embodiments, the pH is from about 6 to about 7. The pH of the composition may be adjusted by the addition of a pH-adjusting agent, such as sodium hydroxide.

In one embodiment of the present invention the aqueous pharmaceutical composition is substantially free of chelating agents. In a further embodiment of the present invention, the aqueous pharmaceutical composition is substantially free of EDTA, or pharmaceutically acceptable salts thereof. The aqueous pharmaceutical composition substantially free of chelating agents is used, e.g., in patients for the treatment of conditions including but not limited acetaminophen overdose, as a mucolytic, and for liver failure, various cancers, methacrylonitrile poisoning, reduction of radiocontrast-induced nephropathy, and reduction of reperfusion injury during cardio bypass surgery.

In further embodiments of the invention, the aqueous pharmaceutical composition contains less than 0.05%, less than 0.02%, or no chelating agents. In still other embodiments of the invention, the aqueous pharmaceutical composition contains less than 0.05%, less than 0.02%, or no EDTA or pharmaceutically acceptable salts thereof.

In yet another embodiment of the invention, the aqueous pharmaceutical composition consists of from 10 to 400 mg/mL acetylcysteine (and preferably greater than 200 mg/mL) and an adequate amount of sodium hydroxide, dissolved in deaerated water, to achieve a final pH from 6 to 8.

The present invention also relates to a method and to compositions for reducing side effects caused by currently marketed acetylcysteine products. More particularly, this invention relates to the finding that the administration of an EDTA-free acetylcysteine composition alleviates side effect(s), for example, hypotension, nausea, vomiting, urticaria, facial flushing, pruritis, combinations of the foregoing and the like, associated with currently marketed acetylcysteine formulations containing, for example, chelating agents (e.g., ethylenediaminetetraacetic acid or EDTA).

The present invention also relates to methods and compositions for preventing or reducing the incidence of anaphylactic reaction associated with currently marketed acetylcysteine formulations containing EDTA.

Thus, in accordance with the present invention, there is provided a method for reducing the level of at least one side effect selected from the group consisting of tachycardia, nausea, vomiting, hypotension, pharyngitis, rhinorrhea, rhonci, pruritis, rash, flushing, and anaphylaxis via the administration of an acetylcysteine formulation free of chelating agents via intravenous administration.

In certain other embodiments there is provided a method of administration of a chelate-free acetylcysteine composition with a reduced side effect profile.

There is also provided a method for reducing side effect(s) following the administration of a therapeutically effective amount of the compositions of the present invention to a patient in need thereof comprising the step of administering a therapeutically effective and non-toxic amount of a chelate-free acetylcysteine composition to a patient, wherein the administration of the chelate-free acetylcysteine composition reduces the drug-induced side effects experienced by currently marketed acetylcysteine compositions.

The present invention is further directed in part to a method of treatment, comprising intravenously administering a 300 mg/kg dose of acetylcysteine to a patient in need of treatment with acetylcysteine over 20 hours via a 2-bag infusion regimen comprising a first dose of 200 mg/kg delivered over a time period from about 3 to about 5 hours, preferably about 4 hours, followed by a second dose of 100 mg/kg over 16 hours. In certain preferred embodiments, the method further comprises determining if the patient has achieved clinically significant improvement in liver function over the course of the 20 hour treatment, and if not, continuing the administration of acetylcysteine to the patient beyond 21 hours to achieve significant clinical improvement in liver function. In certain preferred embodiments where it is desirable to continue acetylcysteine treatment after 21 hours (e.g., where the patient has not achieved sufficient improvement in liver function), the method further comprises administering to the patient either a repeat course of the entire treatment protocol (300 mg/kg over 21 hours) or a repeat course of the maintenance dose (100 mg/kg over 16 hours), and in certain preferred embodiments providing an acetylcysteine infusion at 6.25 mg/kg per hour beyond 21 hours.

The present invention is further directed in part to an improvement in a method of intravenously administering a 300 mg/kg dose of acetylcysteine to a patient in need of treatment with acetylcysteine over 20 hours, the improvement comprising decreasing the initial rate of acetylcysteine infusion to 50 mg/kg per hour and maintaining that rate of infusion for 4 hours. In preferred embodiments, the method further comprises thereafter intravenously delivering a second dose of 100 mg/kg acetylcysteine to the patient over 16 hours. In certain preferred embodiments, the method further comprises determining if the patient has achieved clinically significant improvement in liver function over the course of the hour treatment, and if not, continuing the administration of acetylcysteine to the patient beyond 21 hours to achieve significant clinical improvement in liver function. In certain preferred embodiments where it is desirable to continue acetylcysteine treatment after 21 hours (e.g., where the patient has not achieved sufficient improvement in liver function), the method further comprises administering to the patient either a repeat course of the entire treatment protocol (300 mg/kg over 21 hours) or a repeat course of the maintenance dose (100 mg/kg over 16 hours), and in certain preferred embodiments providing an acetylcysteine infusion at 6.25 mg/kg per hour beyond 21 hours.

The invention is further directed to a pharmaceutical composition consisting of 6 g acetylcysteine, an effective amount of sodium hydroxide to provide a pH in the range from about 6.0 to about 7.5, and a sufficient amount of sterile water for injection, USP to provide a suitable total volume. In certain embodiments, the total volume is 30 mL (200 mg/mL). In certain preferred embodiments, the pharmaceutical composition is packaged in 30-mL glass vials. In other preferred embodiments, the pharmaceutical composition is packages in a container containing from about 30 to about 90 mL of the pharmaceutical composition. In yet other preferred embodiments, the pharmaceutical composition is packaged in ampoules containing from about 1 mL to about 45 mL of the pharmaceutical composition.

The invention is further directed to a pharmaceutical composition consisting of an amount of acetylcysteine effective to provide a therapeutically effective dose of acetylcysteine to a human patient, an effective amount of sodium hydroxide to provide a pH in the range from about 6.0 to about 7.5 (and in certain embodiments a pH from about 6.0 to about 7.0), sterile water for injection, and sodium chloride.

The invention is further directed to a pharmaceutical composition consisting of an amount of acetylcysteine effective to provide a dose of 200 mg per kg of weight of a human patient, an effective amount of sodium hydroxide to provide a pH in the range from about 6.0 to about 7.5, sterile water for injection, in 1000 mL 0.45% Sodium Chloride Injection.

The invention is further directed to a pharmaceutical composition, consisting of an amount of acetylcysteine effective to provide a dose of 100 mg per kg of weight of a human patient, an effective amount of sodium hydroxide to provide a pH in the range from about 6.0 to about 7.5, sterile water for injection, in 500 mL 0.45% Sodium Chloride Injection. In certain preferred embodiments, the pharmaceutical composition contains from about 10 to about 400 mg/mL acetylcysteine.

The term "therapeutically effective" amount or dose means that amount of a drug or pharmaceutical agent that will elicit the biological or medical response of a tissue, system, animal or human that is being sought by a researcher or clinician.

Another embodiment of the present invention is a method of making an aqueous pharmaceutical composition comprising acetylcysteine, wherein the pH of the composition is from 6 to 8 and wherein the composition contains less than 0.05% chelating agents or is substantially free of chelating agents, such as EDTA.

Still other embodiments of the present invention are to methods of treating acetaminophen overdose, liver failure, various cancers, methacrylonitrile poisoning, reduction of radiocontrast-induced nephropathy, reduction of reperfusion injury during cardio bypass surgery, and diseases where a mucolytic is desired comprising administering an aqueous pharmaceutical composition comprising acetylcysteine, wherein the pH of the composition is from 6 to 8 and wherein the composition contains less than 0.05% chelating agents or is substantially free of chelating agents, such as EDTA.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

DETAILED DESCRIPTION OF THE INVENTION

Acetylcysteine administration has been shown to reduce the extent of liver injury following acetaminophen overdose. Acetylcysteine is the nonproprietary name for the N-acetyl derivative of the naturally occurring amino acid, L-cysteine (also known as N-acetyl-L-cysteine and NAC). In one embodiment of the invention, the aqueous compositions of the invention comprise an effective amount of acetylcysteine. Acetylcysteine includes derivatives of acetylcysteine, and pharmaceutically acceptable salts thereof. Derivatives of acetylcysteine include, but are not limited to, esters, amides, anhydrides, and thio-esters and thio-ethers of the sulfhydryl moiety. Pharmaceutically acceptable salts of acetylcysteine and acetylcysteine derivatives include, but are not limited to, sodium salts, potassium salts, magnesium salts, calcium salts, zinc salts, and ammonium salts.

Currently approved acetylcysteine formulations include Acetadote® (commercially available from Cumberland Pharamaceuticals, Inc.) and Parvolex® (commercially available from GSK). Each of the injectable acetylcysteine products used worldwide contain 20% (200 mg/mL) acetylcysteine and 0.05% (0.5 mg/mL) disodium EDTA in water for injection with sodium hydroxide used to adjust pH (6.0-7.5). EDTA is included as an inactive ingredient to enhance product stability and is not thought to affect the activity of acetylcysteine and is not thought to contribute to efficacy in the treatment of acetaminophen overdose. EDTA is a chelating agent, and human exposure to EDTA has been associated with allergic reactions and other side effects.

The present invention is directed in part to new acetylcysteine formulations and a method of treating acetaminophen overdose and reducing side effects associated with currently manufactured acetylcysteine compositions comprising administering to a patient in need thereof an effective amount of a pharmaceutical composition comprising an aqueous solution of acetylcysteine, wherein the composition is substantially free of or contains less than 0.05% EDTA, or pharmaceutically acceptable salts thereof. Other conditions alleviated by the aqueous acetylcysteine compositions of the invention include, but are not limited to, liver failure, various cancers, methacrylonitrile poisoning, reduction of radio contrast induced nephropathy, reduction of reperfusion injury during cardio bypass surgery, and diseases where a mucolytic is desired.

The amount of acetylcysteine may vary depending on the desired characteristics of the solution and can be determined by one of ordinary skill in the art. In one embodiment of the invention, the acetylcysteine comprises 0.1-50%, in another embodiment 1.0-25%, in an additional embodiment 10%, and in yet another embodiment 20% of the solution.

As noted in the Acetadote product label, adverse reactions to Acetadote most commonly occur during the initial loading dose. Adverse reactions during the initial infusion may be derived in part from the concurrent intravenous delivery of a large amount of acetylcysteine (150 mg/kg per hour) and EDTA (0.375 mg/kg per hour). One aspect of the present invention relates to the discovery that EDTA is not necessary for product stability, and to the development of an EDTA-free formulation, acetylcysteine injection. It has been discovered that liquid compositions of acetylcysteine can be produced with pharmaceutically acceptable stability in solution of at least 30 months, and in certain embodiments about three years, at ambient conditions and six months at accelerated conditions (40° C.) without the need of a chelating agent. This stability is surprising given the generally unstable nature of acetylcysteine.

It is hypothesized that these chelate-free acetylcysteine compositions will still provide the necessary therapeutic effect while reducing the side effects associated with currently marketed acetylcysteine compositions that contain chelating agents.

Chelating agents, or chelators, are organic agents that bond with and thereby sequester free metal ions from solution. A widely used chelator is edetic acid or ethylenediaminetetraacetic acid, commonly referred to as EDTA. Additional examples of chelating agents include, but are not limited to, diethylenetriaminepentaacetic acid (DTPA), triethylenetetraaminehexaacetic acid (TTHA), trans-1,2-diaminocyclohexane-N,N,N',N'-tetraacetic acid (CDTA), ethylenediaminedisuccinic acid (EDDS), dihydroxyethyl glycine, citric acid, succinic acid, and tartaric acid A chelator may be used in its acid form, but it may also be used as one of its salts. Salts of EDTA, for example, include edetate calcium disodium, edetate disodium, edetate sodium, edetate trisodium, and edetate dipotassium.

In one embodiment, the compositions of the invention contain no chelating agents or are substantially free of chelating agents, such as EDTA. In another embodiment the compositions of the invention contain less than 0.05% of a chelating agent, such as EDTA. For example, the composition of the present invention may contain less than 0.050%, 0.045%, 0.040%, 0.035, 0.030%, 0.025%, 0.020%, 0.015%, 0.010%, 0.0050%, 0.0025%, 0.0010% of chelating agents, such as EDTA.

The present invention is thus directed in part to liquid compositions of acetylcysteine which are substantially free of or contain less than 0.05% chelating agents, which have a pH that is suitable for injection or inhalation and can also be used orally. Another embodiment of the invention is a pharmaceutical composition comprising an aqueous solution of acetylcysteine, wherein the pH of the composition is from 5 to 9. In yet another embodiment of the invention, the pharmaceutical composition comprises an aqueous solution of acetylcysteine, wherein the pH of the composition is from 6 to 8. A further embodiment of the invention is a pharmaceutical composition comprising an aqueous solution of acetylcysteine, wherein the pH is about 6.8. In still other embodiments, the pH of the composition is 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0.

Formulations of the present invention may further comprise pH-adjusting agents, for example, basic agents. Such agents include a number of inorganic or organic bases which are pharmaceutically acceptable, in the dosage ranges used, including a monovalent metal alkali and/or a divalent metal alkali, such as, for example, sodium hydroxide solution, potassium hydroxide solution, calcium hydroxide, magnesium hydroxide, ammonia, tertiary sodium phosphate, diethanolamine, ethylenediamine, N-methylglucamine, or L-lysine and/or mixtures thereof. In one embodiment of the invention sodium hydroxide is added to the composition to adjust the pH of the composition.

The amount of pH-adjusting agent may vary depending on the desired pH of the composition and the amount of acetylcysteine in the solution and can be determined by one of ordinary skill in the art. For example, in general, the amount of a pH-adjusting agent, such as sodium hydroxide, in formulations of the present invention will directly vary depending on the desired concentration of the acetylcysteine. The exact amount of pH-adjusting agent to be employed will depend on the particular agent and upon the buffering capacity of the aqueous medium and other components of the formulation employed. Thus, the artisan will appreciate that the optimum amount of pH-adjusting agent will be readily determined, for example, by a process of titration to the desired pH.

The present invention also provides for an aqueous pharmaceutical composition consisting of from about 10 to about 400 mg/mL acetylcysteine (and in certain preferred embodiments from about 200 mg/mL to about 400 mg/mL) and the titrated amount of sodium hydroxide or other base, dissolved in deaerated water, to achieve the desired pH of the composition, for example from about 6 to about 8 (and in certain preferred embodiments a pH from about 6 to about 7).

In certain embodiments, the pharmaceutical composition may contain formulation materials for modifying, maintaining or preserving, for example, osmolarity, viscosity, clarity, color, isotonicity, odor, sterility, rate of dissolution or release, adsorption or penetration of the composition. In certain embodiments, suitable formulation materials include, but are not limited to, antioxidants (such as ascorbic acid or sodium metabislfuite); bulking/caking agent (such as mannitol, lactose, or trehalose); excipients and/or pharmaceutical adjuvants. (Remington's Pharmaceutical Sciences, 18th Edition, A. R. Gennaro, ed., Mack Publishing Company (1990).

Administration of the chelate-free compositions provides for a reduction of side effects such as, but not limited to, tachycardia, nausea, vomiting, pharyngitis, rhinorrhea, rhonci, pruritis, rash, flushing, anaphylaxis and any combinations thereof.

The pharmaceutical compositions of the invention may be administered by injection (intravenous or intramuscular), by inhalation, or by the oral route. In one embodiment of the invention, the composition of the invention is dissolved in an aqueous solution containing at least one of dextrose and sodium chloride prior to administration. In another embodiment of the invention, the composition of the invention is dissolved in an aqueous solution of 0.45% or 0.90% sodium chloride (half normal and normal saline respectively). In yet another composition of the invention, it is dissolved in an aqueous solution of 5% dextrose prior to administration. The composition of the invention may also be dissolved in water for injection prior to administration. Other diluents known to those of ordinary skill in the art can also be used. Dosages of the pharmaceutical composition range from 10 mg per dose to as much as 400 mg/kg of acetylcysteine in the pharmaceutical composition and can be determined by one of ordinary skill in the art.

In one embodiment the invention, the pharmaceutical composition is administered to treat (prevent or lessen) hepatic injury after ingestion of a potentially hepatotoxic quantity of acetaminophen (acetaminophen toxicity). In one embodiment, the acetylcysteine formulations of the present invention are administered in a convention (known) manner; in such embodiments, the composition of the invention is mixed in 5% dextrose and 150 mg/kg of drug is given over a period of 15 minutes to 2 hours as a loading dose immediately followed by a second dose at 50 mg/kg over 4 hours and then by a third dose of 100 mg/kg over 20 hours. Additional courses can be given if required.

In particular, the current infusion regimen involves delivery of 300 mg/kg in a 3-bag infusion regimen over 21 hours. The amount of product used is determined by the weight of the subject. This current infusion regimen consists of 150 mg/kg over 1 hour; 50 mg/kg over the next 4 hours; and then 100 mg/kg over the next 16 hours. As noted previously, adverse reactions during the initial infusion may derive in part from the concurrent intravenous delivery of a large amount of acetylcysteine (150 mg/kg per hour) and EDTA (0.375 mg/kg per hour).

In accordance with a further preferred embodiment, the invention is directed to the delivery of acetylcysteine (preferably in a dose of about 300 mg/kg) in a modified 2-bag infusion regimen. The amount of product to be used will still be determined by the weight of the subject. In the modified 2-bag infusion regimen, the dose will still be, e.g., 300 mg/kg dosed over 20 hours but with the first dose of 200 mg/kg delivered over 4 hours, followed by the second dose of 100 mg/kg over 16 hours. The modified infusion regimen decreases the initial rate of acetylcysteine infusion to 50 mg/kg per hour and maintains that rate of infusion for 4 hours. Compared to the 3-bag infusion regimen, the modified 2-bag infusion regimen provides the equivalent dose of the first 2 bags of the current method which is delivered over 5 hours to a single bag delivered over 4 hours. Thus, the first 2 bags of the 3-bag, 5-hour regimen are collapsed into a single bag infused over 4 hours in the modified regimen. The subsequent infusion of acetylcysteine (100 mg/kg) is delivered in 16 hours with the second bag of acetylcysteine in the modified regimen, instead of 16 hours with the third bag of acetylcysteine.

In some cases of acetaminophen overdose, continuation of acetylcysteine beyond 21 hours may be required to achieve significant clinical improvement in liver function. The decision to extend acetylcysteine treatment is a clinical judgment as there is no "standard of care." While limited information is available regarding the safety and efficacy of continuing acetylcysteine therapy beyond 21 hours, no adverse consequences have been reported. In certain preferred embodiments, it is further contemplated that the patients who do not meet the specified clinical endpoints at the end of therapy will receive treatment beyond the indicated 21 hours. In such embodiments, the method further includes administering to the patient either a repeat course of the entire treatment protocol (300 mg/kg over 21 hours) or a repeat course of the maintenance dose (100 mg/kg over 16 hours). There is no standard of care for extending treatment. While limited information is available regarding the safety and efficacy of continuing acetylcysteine therapy beyond 21 hours, no adverse consequences have been reported. Cases receiving treatment beyond the indicated 21 hours to achieve significant improvement are often continued with acetylcysteine infusion at 6.25 mg/kg per hour, or a repeat course of treatment.

One of skill in the art will recognize that the appropriate dosage of the aqueous acetylcysteine compositions may vary depending on the individual being treated and the purpose. For example, the age, body weight, and medical history of the individual patient may affect the efficacy of the therapy. Further, a lower dosage of the composition may be needed to treat, for instance, lower weight patients, while heavier patients require a higher dose of acetylcysteine. A competent physician can consider these factors and adjust the dosing regimen to ensure the dose is achieving the desired therapeutic outcome without undue experimentation. It is also noted that the clinician and/or treating physician will know how and when to interrupt, adjust, and/or terminate therapy in conjunction with individual patient response.

All references cited herein are incorporated herein by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supersede and/or take precedence over any such contradictory material.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

All numbers expressing percentages of ingredients, components, and so forth used in the specification and claims are to be understood as being modified in all instances by the term "w/v." Accordingly, unless indicated to the contrary, the percentages set forth in the specification and attached claims are expressed in weight per unit volume.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the claims.

DETAILED DESCRIPTION OF THE PREFERRED EMBODIMENTS

The following examples represent specific embodiments of the foregoing discovery, and they are not representative of the entire scope of the invention. The acetylcysteine, water, sodium hydroxide, and disodium edetate are Pharmacopeia grade but other pharmaceutically acceptable materials can be utilized.

EXAMPLES

The following examples are offered for illustrative purposes only.

Example 1

Preparation of an Acetylcysteine Formulation

Twenty kilograms of acetylcysteine were added to approximately 60 liters of deaerated water for injection and the solution was mixed. A solution of sodium hydroxide was added to adjust the pH to approximately 6.5 to 7.0 and mixed until dissolved. A sufficient quantity of deaerated water for injection was added to make a 20% solution (total volume of 100 liters). Exposure to air was minimized by displacing oxygen with nitrogen. The solution was passed through a 0.2 micron sterilizing filter. The product was filled into vials (although ampules could also be utilized) and exposure to oxygen minimized by displacing the headspace with nitrogen.

Example 2

Preparation of an Acetylcysteine Formulation

Add 10 kg of acetylcysteine to approximately 60 liters of deaerated water for injection and mix. Add a solution of sodium hydroxide to adjust the pH to approximately 6.5 to 7.0 and continue mixing until dissolved. Add a sufficient quantity of deaerated water for injection to make a 10% solution (total volume of 100 liters). Minimize exposure to air by displacing oxygen with nitrogen or other pharmaceutically inert gas. Pass the solution through a 0.2 micron or other sterilizing filter. Fill the product into vials or ampules minimizing exposure to oxygen by displacing the headspace with nitrogen or other pharmaceutically inert gas.

Example 3

Stability of Acetylcysteine Compositions of the Invention

To determine whether the stability of acetylcysteine solutions required EDTA, three solutions containing different concentrations of edetate disodium were manufactured. The stability of a solution containing 0.05% edetate disodium, a solution containing 40% of that amount, 0.02% edetate disodium, and a solution containing no edetate disodium (0.00%) was examined. The three solutions were manufactured using similar processes to the process described in Example 1. Briefly, the edetate disodium, if any, was added in approximately 60% of the required deaerated water and mixed until dissolved. Acetylcysteine was then added and mixed until dissolved. The pH was adjusted to approximately 6.8 with sodium hydroxide and deaerated water was added to the target level. Nitrogen was used to purge the solutions. The product was then passed through a 0.2 micron filter to remove potential microbial contamination and was filled into vials.

At an initial time point, high performance liquid chromatography (HPLC) was used to assess the acetylcysteine content and chromatographic purity of the three solutions. Measurements were taken of various impurities including, L-cysteine, impurity C, (disulfide), impurity D, and other impurities or degradation products. The peak areas for these HPLC measurements are presented in Table 1. An analysis of unknown peaks in the chromatograms was also undertaken. The "highest unknown" represents the area of the highest individual unidentified peak in the chromatogram, while "total unknowns" represents the total area of unidentified peaks in the chromatogram. See Table 1. In addition to HPLC, the visual appearance, pH, and levels of particulates of each of the three solutions were examined. Vials containing the three solutions were then placed at either 25° C. or 40° C. and vials were removed at 3 months, 6 months, 12 months, 24 months, 30 months and 36 months and assayed for the parameters described above. See Table 1.

Appearance, pH, and particulate matter remained constant over time between the three formulations. Results of the 36-month comparison indicated that stability of acetylcysteine is independent of the EDTA concentration at both 25° C. and 40° C. Appearance, content, and pH remained unchanged and consistent between the three formulations. The impurity levels between the 3 formulations appeared similar at both 25° C. and 40° C. In summary, EDTA did not appear to enhance stability of acetylcysteine in the three formulations, including the EDTA-free formulation. As shown in Table 1, there were no significant differences between each of the three solutions in acetylcysteine content or purity. The results demonstrate that EDTA is not required to produce a product with pharmaceutically acceptable stability. These results are surprising given the generally unstable nature of acetylcysteine.

regimen to lower chances of delayed or missed bags and may also help to decrease adverse events.

The primary outcome of this study is the non-inferiority of efficacy determined by the proportion of subjects who develop hepatotoxicity when treated with AcetadoteEF and the proposed new dosing regimen compared to the rate of hepatotoxicity with Acetadote and the current dosing regimen.

Secondary outcome measures of this study include:
Evaluation of the incidence of clinical need for therapy beyond the current 21 hour FDA approved dosing regimen.
Evaluation of the outcome of subjects receiving continued therapy.
Evaluation of the incidence of treatment-emergent adverse events (AEs).
Evaluation of the incidence of anaphylactoid reactions.

This study is designed to enroll a patient population of, e.g., up to about 200 patients (male and female) ≥12 years old requiring treatment with acetylcysteine for acute acetaminophen toxicity.

TABLE 1

| Time-point | Disodium EDTA | Temp | Acetylcysteine content | L-Cysteine | Impurity C (disulfide) | Impurity D | Highest Unknown | Total Unknown |
|---|---|---|---|---|---|---|---|---|
| Initial | 0.00% | N/A | 202.4 | 0.15 | 0.55 | 0.18 | 0.01 | 0.02 |
| Initial | 0.02% | N/A | 203.9 | 0.19 | 0.44 | 0.23 | 0.03 | 0.05 |
| Initial | 0.05% | N/A | 204.7 | 0.20 | 0.50 | 0.30 | 0.04 | 0.10 |
| 3 months | 0.00% | 25° C. | 204.2 | 0.181 | 0.482 | 0.137 | 0.053 | 0.080 |
| 3 months | 0.00% | 40° C. | 201.8 | 0.370 | 0.540 | 0.90 | 0.070 | 0.132 |
| 3 months | 0.02% | 25° C. | 204.9 | 0.259 | 0.436 | 0.191 | 0.074 | 0.141 |
| 3 months | 0.02% | 40° C. | 204.5 | 0.463 | 0.467 | 0.142 | 0.065 | 0.183 |
| 3 months | 0.05% | 25° C. | 206.1 | 0.299 | 0.444 | 0.214 | 0.044 | 0.119 |
| 3 months | 0.05% | 40° C. | 205.4 | 0.532 | 0.507 | 0.165 | 0.045 | 0.154 |
| 6 months | 0.00% | 25° C. | 202.4 | 0.262 | 0.523 | 0.106 | 0.013 | 0.013 |
| 6 months | 0.00% | 40° C. | 201.7 | 0.707 | 0.509 | 0.053 | 0.133 | 0.133 |
| 6 months | 0.02% | 25° C. | 205.9 | 0.338 | 0.391 | 0.167 | 0.013 | 0.013 |
| 6 months | 0.05% | 25° C. | 207.1 | 0.369 | 0.483 | 0.186 | 0.013 | 0.013 |
| 6 months | 0.05% | 40° C. | 204.6 | 0.932 | 0.509 | 0.104 | 0.135 | 0.135 |
| 6 months | 0.02% | 40° C. | 204.3 | 0.856 | 0.525 | 0.093 | 0.135 | 0.135 |
| 12 months | 0.00% | 25° C. | 204.5 | 0.364 | 0.597 | 0.079 | 0.034 | 0.071 |
| 12 months | 0.02% | 25° C. | 206.0 | 0.435 | 0.475 | 0.134 | 0.042 | 0.130 |
| 12 months | 0.05% | 25° C. | 207.1 | 0.514 | 0.435 | 0.160 | 0.055 | 0.122 |
| 24 months | 0.00% | 25° C. | 193.2 | 0.50 | 0.705 | 0.059 | 0.046 | 0.079 |
| 24 months | 0.02% | 25° C. | 197.5 | 0.64 | 0.636 | 0.116 | 0.046 | 0.078 |
| 24 months | 0.05% | 25° C. | 201.9 | 0.68 | 0.587 | 0.132 | 0.044 | 0.090 |
| 30 months | 0.00% | 25° C. | 205.8 | 0.49 | 0.748 | 0.680 | 0.061 | 0.104 |
| 30 months | 0.02% | 25° C. | 206.3 | 0.64 | 0.611 | 0.121 | 0.064 | 0.131 |
| 30 months | 0.05% | 25° C. | 208.7 | 0.72 | 0.635 | 0.133 | 0.065 | 0.122 |
| 36 months | 0.00% | 25° C. | 202.2 | 0.19 | 0.567 | 0.061 | 0.062 | 0.081 |
| 36 months | 0.02% | 25° C. | 204.2 | 0.25 | 0.534 | 0.098 | 0.063 | 0.126 |
| 36 months | 0.05% | 25° C. | 204.6 | 0.27 | 0.437 | 0.109 | 0.069 | 0.13 |

Example IV

The following study is designed to show the safety and efficacy of EDTA-free acetylcysteine (AcetedoteEF™) and to access the modified 2-bag infusion regimen of the invention as a replacement to the approved 3-bag administration regimen.

This is a multi-center, double-blind, randomized, controlled study to determine the efficacy and safety of a new formulation of acetylcysteine injection.

EDTA is a chelating agent and has been associated with allergic reactions when used in drug product formulations. A new formulation, AcetadoteEF, has been manufactured without the ingredient EDTA. The current product dosed with the approved 21-hour, 3-bag infusion regimen is associated with adverse reactions that are most frequent during the initial 60-minute loading dose of Acetadote. The EDTA-free AcetadoteEF formulation is administered with a modified infusion The test product is Acetadote EF (EDTA-free acetylcysteine) Injection. The reference product is Acetadote (acetylcysteine) Injection. Acetadote EF is packaged as a clear, colorless liquid in 30-mL glass vials, each containing 6 g acetylcysteine in a total volume of 30 mL (200 mg/mL). Acetadote EF contains the following inactive ingredients: sodium hydroxide (used for pH adjustment), and Sterile Water for Injection, USP.

5% Dextrose (D5W), which will be supplied by each site, will be used as the diluent for the Acetadote active drug in this study. ½ Normal Saline (0.45% Sodium Chloride Injection, ½ NS), which will be supplied by each site, will be used as the diluent for the Acetadote EF active drug in this study.

Acetadote (acetylcysteine) Injection is available as a 20% solution in 30 mL (200 mg/mL) single dose glass vials. Acetadote is sterile and can be used for I.V. administration. Acetadote contains the following inactive ingredients: 0.5 mg/mL disodium edetate, sodium hydroxide (used for pH adjustment), and Sterile Water for Injection, USP.

Eligible subjects will be randomized in a 1:1 ratio to receive one of two treatments:

Treatment Group 1: Acetadote: Dose 1 of 150 mg of Acetadote per kg of subject weight in 200 mL 5% Dextrose (D5W) over 60 minutes; followed by Dose 2 of 50 mg of Acetadote per kg of subject weight in 250 mL D5W over the next 4 hours; followed by Dose 3 of 100 mg of Acetadote per kg of subject weight in 500 mL D5W over the next 16 hours.

Treatment Group 2: Acetadote EF: Dose 1 of 200 mg of Acetadote EF per kg of subject weight in 1000 mL 0.45% Sodium Chloride Injection (½ NS) over 4 hours; followed by Dose 2 of 100 mg of Acetadote EF per kg of subject weight in 500 mL ½ NS over the next 16 hours.

The study blind will be maintained by using a double placebo scheme.

To evaluate the primary objective of non-inferiority of efficacy determined by the proportion of subjects who develop hepatotoxicity when treated with Acetadote EF and the proposed new dosing regimen compared to the rate of hepatotoxicity with Acetadote and the current dosing regimen, the following composite endpoint will be measured: The percentage of subjects with an ALT or AST value >1000 U/L versus those with an ALT and AST <1000 U/L.

To evaluate the secondary objective of incidence of clinical need for therapy beyond the current 21 hour FDA approved dosing regimen, the following endpoints will be measured: The percentage of subjects requiring continued therapy, i.e. those who do not meet all of the established clinical endpoints after the initial course of therapy.

To evaluate the secondary objective of outcome of subjects receiving continued therapy, the following endpoint will be measured: The percentage of subjects not experiencing death or liver transplant versus those experiencing death or liver transplant (or need for transplant).

To evaluate the secondary objective of incidence of treatment emergent adverse events, the following endpoint will be measured: The percentage of subjects with treatment emergent adverse events.

To evaluate the secondary objective of incidence of anaphylactoid reactions, the following endpoint will be measured: The percentage of subjects experiencing an anaphylactiod reaction, as defined by the presence of hypotension, edema, urticaria or respiratory symptoms.

Safety will be evaluated on the basis of the following assessments: Vital signs (heart rate, respiratory rate, blood pressure); Clinical chemistry measurements; Treatment-emergent AEs including anaphylactoid reactions at study Hour 1.

The following terms and definitions will be used to characterize a treatment emergent adverse event as an anaphylactoid reaction: Hypotension (adult): SBP either less than or equal to 90 mm Hg or a decrease in the subject's baseline SBP of 40 mm Hg or greater, associated with the infusion of acetylcysteine. Hypotension (pediatric): SBP less than 70+ (age×2). Edema: Presence of any of the following: angioedema, swelling of the lips, tongue and/or around the eyes, or edema, associated with the infusion of acetylcysteine. Urticaria: Presence of any of the following: red rash, itchy rash, redness, flushing of the face, associated with the infusion of acetylcysteine. Respiratory Symptoms: Presence of any of the following: Cough, wheezing, stridor, shortness of breath, chest tightness, respiratory distress, or bronchospasm, associated with the infusion of acetylcysteine.

Should a subject meet the criteria for continued therapy, the subject will receive either an entire repeat course (300 mg/kg) of blinded treatment (whichever treatment to which they were originally randomized) or a repeat of the maintenance dose (100 mg/kg). After a repeat course of treatment, clinical management of the subject will be at the discretion of the treating physician.

In the preceding specification, the invention has been described with reference to specific exemplary embodiments and examples thereof. It will, however, be evident that various modifications and changes may be made thereto without departing from the broader spirit and scope of the invention as set forth in the claims that follow. The specification and drawings are accordingly to be regarded in an illustrative manner rather than a restrictive sense.

What is claimed is:

1. A method of treating acetaminophen overdose-induced liver injury, comprising intravenously administering an acetylcysteine composition to a patient in need thereof via a 2-bag infusion regimen comprising:
    administering a first dosage of 50 mg/kg of acetylcysteine per hour for 4 hours followed by administering a second dosage of 100 mg/kg of acetylcysteine over 16 hours.

2. The method of claim 1, further comprising determining if the patient has achieved clinically significant improvement in liver function over the course of the 2-bag infusion regimen, and continuing the administration of acetylcysteine to the patient beyond 21 hours where the patient has not achieved clinically significant improvement in liver function.

3. The method of claim 1, further comprising intravenously administering to the patient a third dose of 100 mg/kg of acetylcysteine over 16 hours following the second dose.

4. The method of claim 1, further comprising intravenously administering to the patient 6.25 mg/kg of acetylcysteine per hour following the second dose.

5. The method of claim 2, wherein clinically significant improvement in liver function is determined by the ALT level of the patient.

6. The method of claim 1, further comprising repeating the 2-bag infusion regimen following the second dose.

7. The method of claim 1, wherein the acetylcysteine composition contains less than 0.05% EDTA.

8. The method of claim 1, wherein the acetylcysteine composition contains less than 0.05% chelating agents.

9. The method of claim 1, wherein the acetylcysteine composition is prepared in an aqueous solution of at least one of 5% dextrose, 0.45% sodium chloride, 0.90% sodium chloride, and water for injection prior to administration.

10. The method of claim 2, wherein clinically significant improvement in liver function is determined by the AST level of the patient.

11. The method of claim 1, wherein the patient is in liver failure.

12. A method of treating acetaminophen overdose, comprising intravenously administering an acetylcysteine composition to a patient in need thereof via a 2-bag infusion regimen comprising:
    administering a first dosage of 50 mg/kg of acetylcysteine per hour for 4 hours followed by administering a second dosage of 100 mg/kg of acetylcysteine over 16 hours.

13. The method of claim 12, further comprising determining if the patient has achieved clinically significant improvement in liver function over the course of the 2-bag infusion regimen, and continuing the administration of acetylcysteine to the patient beyond 21 hours where the patient has not achieved clinically significant improvement in liver function.

14. The method of claim 12, further comprising intravenously administering to the patient a third-dose of 100 mg/kg of acetylcysteine over 16 hours following the second dose.

15. The method of claim 12, further comprising intravenously administering to the patient 6.25 mg/kg of acetylcysteine per hour following the second dose.

16. The method of claim 13, wherein clinically significant improvement in liver function is determined by the ALT level of the patient.

17. The method of claim 12, further comprising intravenously administering to the patient following the second dose a third dose of 200 mg/kg of acetylcysteine over 4 hours, followed by a fourth dose of 100 mg/kg of acetylcysteine over 16 hours.

18. The method of claim 12, further comprising repeating the 2-bag infusion regimen following the second dose.

19. The method of claim 12, wherein the acetylcysteine composition contains less than 0.05% EDTA.

20. The method of claim 12, wherein the acetylcysteine composition contains less than 0.05% chelating agents.

21. The method of claim 12, wherein the acetylcysteine composition is prepared in an aqueous solution of at least one of 5% dextrose, 0.45% sodium chloride, 0.90% sodium chloride, and water for injection prior to administration.

* * * * *